United States Patent [19]
Clitherow et al.

[11] Patent Number: 5,221,688
[45] Date of Patent: Jun. 22, 1993

[54] IMIDAZOLE DERIVATIVES

[75] Inventors: John W. Clitherow, Sawbridgeworth; Eric W. Collington, Knebworth, both of England

[73] Assignee: Glaxo Group Limited, London, England

[21] Appl. No.: 690,302

[22] Filed: Apr. 24, 1991

[30] Foreign Application Priority Data

Apr. 25, 1990 [GB] United Kingdom ............... 9009240

[51] Int. Cl.$^5$ ................ C07D 233/64; A61K 31/415
[52] U.S. Cl. .......................... 514/400; 548/336.5; 548/109; 514/338; 514/399
[58] Field of Search ............... 548/101, 109, 342; 514/338, 400

[56] References Cited

U.S. PATENT DOCUMENTS

| | | | |
|---|---|---|---|
| 4,956,466 | 9/1990 | Vinas | 548/101 |
| 4,965,365 | 10/1990 | Sanfeliu et al. | 548/109 |
| 5,008,256 | 4/1991 | Clitherow | 514/184 |

FOREIGN PATENT DOCUMENTS

| | | |
|---|---|---|
| 0350422 | 1/1990 | European Pat. Off. . |
| 0351348 | 1/1990 | European Pat. Off. . |
| 0387177 | 9/1990 | European Pat. Off. . |
| 8804023 | 10/1989 | Spain . |
| 8900857 | 3/1990 | Spain . |
| 2218987A | 11/1989 | United Kingdom . |

OTHER PUBLICATIONS

Cho, *Drug Development Research*, 17:185–197 (1989).
Escolar et al., *Drugs Exptl. Clin. Res.*, XV(2) 83–89 (1989).

*Primary Examiner*—Nicholas S. Rizzo
*Attorney, Agent, or Firm*—Bacon & Thomas

[57] ABSTRACT

The invention relates to salts formed between basic $H_2$-receptor antagonists and a complex of zinc with a carboxylic acid selected from tartaric acid, citric acid and alkyl citric acids, and to solvates of such salts, excluding salts in which the basic $H_2$-receptor antagonist is ranitidine. Examples of basic $H_2$-receptor antagonists are cimetidine, famotidine, nizatidine and roxatidine.

The salts are useful in the treatment of gastrointestinal disorders, such as peptic ulcer disease and non-ulcer dyspepsia.

6 Claims, No Drawings

IMIDAZOLE DERIVATIVES

This invention relates to salts of compounds having antagonist activity at histamine $H_2$-receptors, to a process for the preparation thereof, to pharmaceutical compositions containing them and to their use in therapeutics. More particularly the invention is concerned with salts of histamine $H_2$-receptor antagonists formed with zinc complexes of certain carboxylic acids.

Compounds which have antagonist activity at histamine $H_2$-receptors are used in the treatment of conditions where there is an advantage in lowering gastric acidity. Such conditions include duodenal and gastric ulceration, reflux oesophagitis and Zollinger-Ellison syndrome. Ranitidine may also be used prophylactically in surgical procedures, and in the treatment of allergic and inflammatory conditions where histamine is a known mediator.

UK Patent Specification No. 2218987A, European Patent Specifications Nos. 350422 and 351348, and Spanish Patent Specifications Nos. 8804023 and 8900857 disclose zinc derivatives of the histamine $H_2$-receptor antagonists cimetidine, etintidine, nizatidine, zaltidine and ranitidine, covered by the general formula

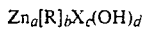

$$Zn_a[R]_b X_c(OH)_d$$

where R is respectively cimetidine, etintidine, nizatidine, zaltidine or ranitidine, X is an anion of a pharmaceutically acceptable acid, a is an integer from 1 to 5, and b is an integer from 1 to 7. According to UK Specification No. 2218987A, c is an integer from 1 to 4, and d is 2a-c. According to European Specifications Nos. 350422 and 351348, and Spanish Specifications Nos. 8804023 and 8900857, c is zero or an integer from 1 to 4, and d is 2a-c for monovalent acid anions, a-c for divalent acid anions and zero or 2 when c is zero. Such compounds are described as having antiulcer properties.

Zinc compounds such as zinc chloride, zinc sulphate and zinc acexamate have been described in for example Drug Development Research 17, 185-197 (1989) and Drugs Exptl. Clin. Res. XV(2), 83-89 (1989) as being gastrohepatic protective agents, having a stabilising action on mast cells, preserving gastric mucus and protecting the gastric mucosa against the actions of known gastric irritants. Such zinc compounds thus have a role in the treatment of gastric ulceration.

The only known stable form of zinc citrate is the 3:2 complex formed between zinc and citric acid $Zn_3(C_6H_5O_7)_2.2H_2O$, and this has been incorporated into toothpaste preparations as an antibacterial and antiplaque agent.

It has now surprisingly been found that basic $H_2$-receptor antagonists will form stable salts with a simple 1:1 stoichiometric complex of zinc and a carboxylic acid such as citric acid, and that the salts thus formed possess a useful and advantageous profile of activity.

The present invention thus provides novel salts of a basic $H_2$-receptor antagonist and a complex of zinc with a carboxylic acid selected from tartaric acid, citric acid or an alkyl citric acid, and solvates of such salts. Salts in which the $H_2$-receptor antagonist is ranitidine are however excluded from the scope of the invention.

The alkyl citric acid may be for example a $C_{1-6}$ alkyl citric acid, more particularly a $C_{1-3}$ alkyl citric acid (e.g. propylcitric acid).

In instances where the carboxylic acid can exhibit optical and/or geometrical isomerism, the invention is intended to include all optical isomers including racemates, and/or geometric isomers. Solvates, including hydrates, are also included within the scope of the invention.

The preferred carboxylic acid for use in the invention is citric acid.

Suitable basic histamine $H_2$-receptor antagonists for salt formation with zinc-carboxylic acid complexes according to the invention include imidazole derivatives; substituted aminoalkylbenzene, furan and thiazole derivatives (e.g. dimethylaminomethyl-furanyl-methylthioethylamino compounds, piperidinomethylphenoxypropylamino compounds and dimethylaminomethylthiazolylmethylthioethylamino compounds); guanidinothiazolyl derivatives including guanidinothiazolyl-methylthioethyl and guanidinothiazolylmethylthioethylamino compounds; and guanidinopyrazolyl derivatives. Examples of particular basic histamine $H_2$-receptor antagonists are cimetidine, famotidine, roxatidine, niperotidine, nizatidine, mifentidine, zaltidine, ebrotidine, bisfentidine, 3-amino-4-[[3-[3-(1-piperidinylmethyl)phenoxy]propyl]amino]-3-cyclobutene-1,2-dione (BMY 25368), 5-[3-[2-(2,2,2-trifluoroethyl)-guanidino]pyrazol-1-yl]valeramide, and N-ethyl-N'-[3-(3-piperidinomethylphenoxy)propyl]urea.

Particular basic $H_2$-receptor antagonists for use according to the invention are cimetidine, famotidine, nizatidine and roxatidine.

Cimetidine represents a preferred basic $H_2$-receptor antagonist for use according to the invention.

A preferred salt according to the invention is N-cyano-N'-methyl-N''-[2-[[(5-methyl-1H-imidazol-4-yl)methyl]thio]ethyl]guanidine 2-hydroxy-1,2,3-propanetricarboxylate zinc (2+) complex, more specifically a 1:1 complex, also known as cimetidine zinc citrate.

Salts according to the invention possess a particularly advantageous combination of properties for the treatment of gastrointestinal disorders, especially peptic ulcer disease and other gastroduodenal conditions, for example non-ulcer dyspepsia.

Salts according to the invention possess antisecretory and cytoprotective properties. Antisecretory activity may be demonstrated in vivo against histamine-induced gastric acid secretion in the Heidenhain pouch dog. Cytoprotective activity has been demonstrated in vivo by the ability of the salts to inhibit ethanol-induced gastric lesions in rats.

A further feature of salts according to the invention is that they are water soluble and give stable aqueous solutions.

The salts of the invention are distinct chemical entities, and may be distinguished from simple mixtures of the basic $H_2$-receptor antagonist and a complex formed between zinc and a carboxylic acid. This distinction may be demonstrated on the basis of, for example, infrared spectroscopy.

Salts according to the invention may be prepared by reacting the $H_2$-receptor antagonist with an appropriate zinc-carboxylic acid complex (e.g. zinc citrate) in a suitable solvent such as water, and separating the salt thus formed from the solution.

According to a further aspect the invention provides a salt of a basic $H_2$-receptor antagonist and a complex of zinc with tartaric acid, citric acid, or an alkyl citric acid, including solvates of such salts, said salt being prepared by reacting the H$_2$-antagonist with an appropriate zinc-carboxylic acid complex.

The reaction between the H$_2$-receptor antagonist and an appropriate zinc-carboxylic acid complex to give a salt according to the invention is preferably carried out at a temperature within the range of 20° to 60° C., more preferably at room temperature. The resulting solution is cooled (if appropriate) and filtered or decanted from any residual solid. The required salt may be obtained from the solution, by evaporation followed by extraction and trituration of the resulting residue using for example an alcohol e.g. methanol or ethanol, a ketone e.g. acetone and/or an ether e.g. diethyl ether.

The intermediate zinc-carboxylic acid complex may be prepared by reacting a zinc base (e.g. zinc oxide or zinc carbonate) with an appropriate carboxylic acid (e.g. citric acid) in a solvent such as water, conveniently at a temperature within the range of 20° to 40°.

The intermediate zinc-carboxylic acid complex is preferably formed in situ and immediately reacted with the H$_2$-antagonist to give a salt according to the invention.

The salts according to the invention may be formulated for administration in any convenient way and the invention includes within its scope pharmaceutical compositions containing a salt according to the invention adapted for use in human or veterinary medicine. Such compositions, which are primarily intended for oral administration, may be formulated in a conventional manner using one or more pharmaceutically acceptable carriers or excipients.

For oral administration, the pharmaceutical compositions may take the form of, for example, tablets (including chewable or suckable tablets) or capsules (of either the hard or soft type). Such compositions may be prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Tablets represent a preferred type of composition for oral use.

The dose at which the salts of the invention may be administered to man will depend upon the nature of the histamine H$_2$-receptor antagonist, and the salts may in general be administered at doses based on the normal dosage range at which the H$_2$-receptor antagonist concerned is therapeutically effective. Thus a suitable dosage of a salt of a zinc-carboxylic acid complex in which the H$_2$-receptor antagonist is cimetidine may be for example 400 mg to 1.6 g per unit dose. Similarly, for famotidine 15 to 80 mg (more preferably 30 to 80 mg), for nizatidine 80 to 500 mg, and for roxatidine 80 to 500 mg.

The unit dose may be administered, for example, one to four times daily, preferably once or twice. The exact dose will depend on the nature and severity of the condition being treated, and it will also be appreciated that it may be necessary to make routine variations to the dosage depending on the age and weight of the patient.

The invention is illustrated by the following Example in which temperatures are in °C. Thin layer chromatography (t.l.c.) was carried out on silica, eluting with the solvent system indicated, and using u.v., iodoplatinate, potassium permanganate and bromocresol green stain for detection.

EXAMPLE

N-Cyano-N'-methyl-N''-[2-[[(5-methyl-1H-imidazol-4-yl)methyl]thio]ethyl]guanidine[2-hydroxy-1,2,3-propanetricarboxylate zinc (2+) complex (1:1)](1:1)["Cimetidine zinc citrate"(1:1:1)].

Zinc oxide (1.63 g) was dissolved in a solution of 2-hydroxy-1,2,3-propanetricarboxylic acid (citric acid, 4.2 g) in water (25 ml at room temperature. A slight exothermic reaction occurred and after all the zinc oxide had dissolved, the solution was filtered and N-cyano-N'-methyl-N''-[2-[[(5-methyl-1H-imidazol-4-yl)methyl]thio]ethyl]guanidine (cimetidine, 5.05 g) added. The mixture was diluted with water (30 ml) and shaken until almost all the solid had dissolved. The clear supernatant liquid was decanted away from a small amount of residual gum which was discarded and the decanted liquid evaporated to dryness to give a viscous gum. This was evaporated with hot methanol (50 ml) and the residue suspended in hot methanol (100 ml). The suspension was filtered, the residue washed well with hot methanol then ether and dried to give a solid (9.344 g).

A portion of the solid (7.02 g) was mixed with water (50 ml) and the mixture heated to 70° then filtered. The residue was washed with water and the combined filtrates evaporated to dryness in vacuo to give a solid residue which was removed from the flask with the aid of ether. The residue was ground to a powder, then mixed with ether (100 ml) and the mixture filtered. The residue was dried to give the title compound (5.523 g).

T.l.c. (Methylene chloride:ethanol:0.88 ammonia; 50:8:1) Rf 0.35 (cimetidine) and Rf zero (zinc citrate).

Analysis Found: C,37,76; H,4.56; N,16.51; O,22.97; S,6.07; Zn,12.6.

$C_{16}H_{22}N_6O_7SZn:H_2O$; 1:0.38 requires C,37.34; H,4.46; N,16.33; 0,22.94; S,6.23; Zn,12.70%

Water assay indicated 1.36% $H_2O \equiv 0.38$ mole.

The following Examples A to D illustrate pharmaceutical compositions according to the invention in which the active ingredient is in particular cimetidine zinc citrate, famotidine zinc citrate, nizatidine zinc citrate or roxatidine zinc citrate. Other compounds according to the invention may be formulated in a similar manner, using an appropriate amount of active ingredient depending on the compound concerned, with suitable adjustments in the amounts of excipients and weights of the final dosage forms.

EXAMPLE A

Tablets

Tablets may be prepared by the normal methods such as direct compression or wet granulation.

The tablets may be film coated with suitable film forming materials, such as hydroxypropyl methylcellulose, using standard techniques.

| (i) Direct Compression | mg/tablet |
| --- | --- |
| Cimetidine Zinc Citrate | 800 |
| Lactose | 120 |
| Microcrystalline Cellulose | 120 |
| Cross-linked Polyvinylpyrrolidone | 50 |
| Magnesium Stearate | 10 |
| Compression weight | 1100 mg |

The cimetidine zinc citrate, microcrystalline cellulose, lactose and cross-linked polyvinylpyrrolidone are sieved through a 500 micron sieve and blended in a suitable mixer. The magnesium stearate is sieved through a 250 micron sieve and blended with the active blend. The blend is compressed into tablets using suitable punches.

Famotidine zinc citrate may be formulated in a similar manner, using 75 mg of the active ingredient and appropriate weights of the excipients to give a tablet compression weight of 400 mg. Nizatidine zinc citrate and roxatidine zinc citrate may also be formulated in a similar manner, using 290 mg of the active ingredient and appropriate weights of the excipients to give a tablet compression weight of 600 mg.

| (ii) Wet granulation | mg/tablet |
| --- | --- |
| Nizatidine Zinc Citrate | 290 |
| Lactose | 130 |
| Pregelatinised Starch | 50 |
| Cross-linked Polyvinylpyrrolidone | 25 |
| Magnesium Stearate | 5 |
| Compression weight | 500 mg |

The nizatidine zinc citrate, lactose and pregelatinised starch are blended together and granulated with water. The wet mass is dried and milled. The magnesium stearate and cross-linked polyvinylpyrrolidone are screened through a 250 micron sieve and blended with the granule. The resultant blend is compressed using suitable tablet punches.

EXAMPLE B

Suckable/Chewable Tablets

|  | mg/tablet |
| --- | --- |
| Cimetidine Zinc Citrate | 400 |
| Polyvinylpyrrolidone | 100 |
| Sweetner | qs |
| Flavour | qs |
| Magnesium Stearate | 20 |
| Mannitol to | 2000 |
| Compression weight | 2000 mg |

The cimetidine zinc citrate, sweetener, flavour and mannitol are blended together and granulated with a solution of polyvinylpyrrolidone. The wet mass is dried, milled and lubricated with magnesium stearate (meshed through a 250 micron sieve). The resultant granule is compressed into tablets using suitable punches.

Suckable/chewable tablets containing famotidine zinc citrate (75 mg), nizatidine zinc citrate (290 mg) or roxatidine zinc citrate (290 mg) may be prepared in a similar way with appropriate adjustment of the amount of mannitol to retain a compression weight of 2000 mg.

EXAMPLE C

Capsules

|  | mg/capsule |
| --- | --- |
| (i) Cimetidine Zinc Citrate | 400 |
| Pregelatinised Starch | 95 |
| Magnesium Stearate | 5 |
| Fill weight | 500 mg |

The cimetidine zinc citrate and pregelatinised starch are screened through a 500 micron mesh sieve, blended together and lubricated with magnesium stearate (meshed through a 250 micron sieve). The blend is filled into hard gelatin capsules of a suitable size.

|  | mg/capsule |
| --- | --- |
| (ii) Famotidine Zinc Citrate | 75 |
| Lactose | 103 |
| Polyvinylpyrrolidone | 10 |
| Magnesium Stearate | 2 |
| Fill weight | 200 mg |

The famotidine zinc citrate and lactose are blended together and wet massed with a solution of polyvinylpyrrolidone. The mass is dried and milled and blended with the magnesium stearate and cross-linked polyvinylpyrrolidone (screened through a 250 micron mesh). The resultant blend is filled into hard gelatin capsules of a suitable size.

EXAMPLE D

Syrup

| Famotidine Zinc Citrate | 75.0 mg |
| --- | --- |
| Hydroxypropyl Methylcellulose | 22.5 mg |
| Propyl Hydroxybenzoate | 0.75 mg |
| Butyl Hydroxybenzoate | 0.325 mg |
| Saccharin Sodium | 2.5 mg |
| Sorbitol Solution | 0.5 ml |
| Suitable Buffers | qs |
| Suitable Flavours | qs |
| Purified Water to | 5.0 ml |

The hydroxypropyl methylcellulose is dispersed in a portion of hot purified water together with the hydroxybenzoates and the solution is allowed to cool to room temperature. The saccharin sodium, flavours and sorbitol solution are added to the bulk solution. The famotidine zinc citrate is dissolved in a portion of the remaining water and added to the bulk solution. Suitable buffers may be added to control the pH in the region of maximum stability. The solution is made up to volume, filtered and filled into suitable containers.

Syrups containing cimetidine zinc citrate, nizatidine zinc citrate or roxatidine zinc citrate as the active ingredient may be prepared in a similar manner, replacing famotidine zinc citrate with cimetidine zinc citrate (400.0 mg), nizatidine zinc citrate (290.0 mg) or roxatidine zinc citrate (290.0 mg) and making the volume up to 10.0 ml.

We claim:

1. A salt formed between cimetidine and a complex of zinc with a carboxylic acid selected from tartaric acid, citric acid and alkyl citric acids, or a solvate of such a salt, wherein said complex of zinc and said carboxylic acid is a 1:1 complex.

2. A salt according to claim 1, wherein the carboxylic acid is citric acid.

3. The cimetidine zinc citrate complex which is N-cyano-N'-methyl-N''-[2-[[(5-methyl-1H-imidazol-4-yl)methyl]thio]ethyl]guanidine2-hydroxy-1,2,3-propanetricarboxylate zinc (2+) complex and solvates thereof wherein the ratio of zinc to citrate in said complex is 1:1.

4. A process for the preparation of a salt according to claim 1, which comprises reacting cimetidine with a complex of zinc and the carboxylic acid in a suitable solvent and separating the salt thus formed from the solution wherein said complex of zinc and carboxylic acid is a 1:1 complex.

5. A pharmaceutical composition for the treatment of a gastrointestinal disorder comprising an effective amount of a salt according to claim 1, together with at least one pharmaceutically acceptable carrier or excipient.

6. A method of treatment of a gastrointestinal disorder which comprises administering to a human or animal subject an effective amount of a salt according to claim 1 or a solvate of such a salt.

* * * * *